(12) United States Patent
Kim et al.

(10) Patent No.: US 11,358,923 B2
(45) Date of Patent: Jun. 14, 2022

(54) METHOD FOR MANUFACTURING CYCLODODECANONE

(71) Applicant: HANWHA SOLUTIONS CORPORATION, Seoul (KR)

(72) Inventors: Jiyeon Kim, Daejeon (KR); Jeongseok Park, Daejeon (KR); Jinho Park, Daejeon (KR); Kyuho Song, Daejeon (KR)

( * ) Notice: Subject to any disclaimer, the term of this patent is extended or adjusted under 35 U.S.C. 154(b) by 0 days.

(21) Appl. No.: 17/298,921

(22) PCT Filed: Sep. 16, 2019

(86) PCT No.: PCT/KR2019/011907
§ 371 (c)(1),
(2) Date: Jun. 1, 2021

(87) PCT Pub. No.: WO2020/130292
PCT Pub. Date: Jun. 25, 2020

(65) Prior Publication Data
US 2022/0064094 A1      Mar. 3, 2022

(30) Foreign Application Priority Data
Dec. 19, 2018   (KR) .................. 10-2018-0165138

(51) Int. Cl.
*C07C 45/28*          (2006.01)

(52) U.S. Cl.
CPC .......... *C07C 45/28* (2013.01); *C07C 2601/20* (2017.05)

(58) Field of Classification Search
CPC ....................................... C07C 45/28
See application file for complete search history.

(56) References Cited

U.S. PATENT DOCUMENTS

| | | | | |
|---|---|---|---|---|
| 6,828,449 B2 * | 12/2004 | Herwig | ............... | C07D 301/12 549/518 |
| 9,000,223 B2 * | 4/2015 | Micoine | ................... | B01J 23/42 568/341 |
| 9,533,933 B2 * | 1/2017 | Micoine | ................. | C07C 45/82 |
| 9,643,153 B2 * | 5/2017 | Meier | ................. | B01J 19/2475 |

FOREIGN PATENT DOCUMENTS

JP          2004059434 A   *   2/2004

* cited by examiner

*Primary Examiner* — Sikarl A Witherspoon
(74) *Attorney, Agent, or Firm* — Harvest IP Law, LLP

(57) ABSTRACT

The present invention relates to a method of preparing cyclododecanone. According to the present invention, a method of preparing cyclododecanone which allows implementation of a high conversion rate and minimization of production of unreacted materials and reaction by-products may be provided. In addition, the present invention implements a high conversion rate and a high selectivity even by a simplified process configuration, and thus may be usefully utilized in an economical method of preparing laurolactam, allowing commercially easy mass production.

12 Claims, No Drawings

METHOD FOR MANUFACTURING CYCLODODECANONE

CROSS-REFERENCE TO RELATED APPLICATIONS

This application is a National Stage of International Application No. PCT/KR2019/011907 filed Sep. 16, 2019, claiming priority based on Korean Patent Application No. 10-2018-0165138 filed Dec. 19, 2018.

TECHNICAL FIELD

The present invention relates to a method of preparing cyclododecanone.

BACKGROUND ART

Cyclododecanone (CDON) is used for preparing laurolactam, and the laurolactam is an organic compound used as a monomer for preparing polyamide (e.g., nylon-12, nylon 6-12, and the like) which is an engineering plastic.

Cyclododecanone may be prepared generally by starting from cyclododecatriene (CDT). Specifically, cyclododecanone may be prepared by preparing cyclododecene (CDEN) by a selective hydrogenation reaction from cyclododecatriene and then oxidizing cyclododecene.

However, according to the method of preparing cyclododecanone described above, a significant amount of by-products (e.g., cyclododecanol, cyclododecandiol, and the like) are produced.

Thus, since the problem of the conventional technology described above adversely affects construction of a whole process system for preparing laurolactam, a study to find a more efficient way is still needed.

In order to solve the problem of the conventional technology as such, the present inventors conducted in-depth study of an efficient way for a method of preparing cyclododecanone. As a result, the present inventors confirmed that when a form of adding hydrogen peroxide is adjusted in the introduction of an intermediate step using epoxidized cyclododecene as an intermediate, cyclododecanone may be prepared with significantly improved conversion rate and selectivity, thereby completing the present invention.

DISCLOSURE

Technical Problem

An object of the present invention is to provide a preparation method which may produce cyclododecanone with a high conversion rate and a high selectivity.

Another object of the present invention is to provide a method of preparing cyclododecanone which may effectively inhibit decomposition of hydrogen peroxide to increase the selectivity of hydrogen peroxide.

Still another object of the present invention is to provide a method of preparing cyclododecanone which is economical with a more simplified process configuration.

Technical Solution

In one general aspect, a method of preparing cyclododecanone includes: applying heat while additionally injecting hydrogen peroxide to a mixture of cyclododecene and hydrogen peroxide under a catalyst system including a tungsten compound, a phosphoric acid compound, and an amine compound to prepare epoxidized cyclododecane; and preparing cyclododecanone by a rearrangement reaction without separation of a reaction mixture including the epoxidized cyclododecane under an alkaline metal halide catalyst.

In the method of preparing cyclododecanone according to an exemplary embodiment of the present invention, the hydrogen peroxide additionally injected may be injected so that the following relation formula is satisfied:

$50 \leq In_f \leq 150$ $1.0 \leq In_m \leq 3.0$ [Relation Formula]

wherein $In_f$ is an injection flow rate per minute (µl/min) of the hydrogen peroxide additionally injected, and $In_m$ is a mole ratio (B/A) between cyclododecene (A) and hydrogen peroxide additionally injected (B).

In the method of preparing cyclododecanone according to an exemplary embodiment of the present invention, the mixture may include substantially no cyclododecane.

In the method of preparing cyclododecanone according to an exemplary embodiment of the present invention, in the mixture, 1 to 10 parts by weight of hydrogen peroxide is mixed, based on 100 parts by weight of the cyclododecene.

In the method of preparing cyclododecanone according to an exemplary embodiment of the present invention, the tungsten compound may be one or a mixture of two or more selected from a tungstic acid, a tungstate salt, and the like.

In the method of preparing cyclododecanone according to an exemplary embodiment of the present invention, the phosphoric acid compound may be one or a mixture of two or more selected from an inorganic phosphoric acid, an inorganic phosphate salt, an organic phosphoric acid, and the like.

In the method of preparing cyclododecanone according to an exemplary embodiment of the present invention, the amine compound may be one or a mixture of two or more selected from a tertiary amine, a quaternary ammonium salt, and the like.

In the method of preparing cyclododecanone according to an exemplary embodiment of the present invention, 0.01 to 10 parts by weight of the catalyst system may be included, based on 100 parts by weight of the cyclododecene.

In the method of preparing cyclododecanone according to an exemplary embodiment of the present invention, the tungsten compound (a), the phosphoric acid compound (b), and the amine compound (c) in the catalyst system may be mixed at a weight ratio of 1:0.1 to 2.0:0.1 to 5.0.

In the method of preparing cyclododecanone according to an exemplary embodiment of the present invention, the preparing epoxidized cyclododecane may be performed under a temperature condition of 50 to 120° C.

In the method of preparing cyclododecanone according to an exemplary embodiment of the present invention, the rearrangement reaction may be performed without a solvent.

In the method of preparing cyclododecanone according to an exemplary embodiment of the present invention, 0.01 to 10 parts by weight of the alkali metal halide catalyst may be included, based on 100 parts by weight of the epoxidized cyclododecane.

In the method of preparing cyclododecanone according to an exemplary embodiment of the present invention, a conversion rate of the cyclododecene and a conversion rate of the epoxidized cyclododecane may be 90% or more.

Advantageous Effects

According to the present invention, ratios of cyclododecanol, cyclododecandiol, and the like which are obtained as reaction by-products in the final product may be significantly decreased and cyclododecanone may be prepared with a high conversion rate.

In addition, according to the present invention, a separation/purification process for removing the reaction by-products is also not needed. Thus, the present invention may provide a simplified process configuration to provide a method of preparing cyclododecanone allowing commercially easy mass production.

In addition, according to the present invention, the form of adding hydrogen peroxide may be adjusted to effectively inhibit decomposition of hydrogen peroxide itself and to increase the selectivity of hydrogen peroxide.

Thus, the present invention may prevent an explosive reaction by the decomposition of hydrogen peroxide, efficiently control heat of reaction therefrom, and thus, increase process convenience.

BEST MODE

Hereinafter, the method of preparing cyclododecanone according to the present invention will be described, however, technical terms and scientific terms used herein have the general meaning understood by those skilled in the art to which the present invention pertains unless otherwise defined, and a description for the known function and configuration which may unnecessarily obscure the gist of the present invention will be omitted in the following description.

In the present invention, paying attention to the problem of the conventional technology, a method of preparing cyclododecanone which may implement a high conversion rate and a high selectivity with a very economical method will be suggested.

According to the present invention, a high conversion rate is implemented and an additional separation/purification step is not involved due to the minimized production of unreacted materials and reaction by-products, thereby simplifying a process configuration. In addition, according to the present invention, a stable preparation process which maximizes catalyst activity and has no danger of explosion by hydrogen peroxide may be provided.

Thus, according to the present invention, a high conversion rate and a high selectivity are shown, of course, and the process configuration is simplified to be continuously operated, so that the present invention is very advantageous for being applied to real industry.

In the present invention, as mentioned above, when the form of adding hydrogen peroxide is adjusted, unexpected improvement of the conversion rate and selectivity was confirmed, and it was confirmed that it is possible to efficiently prepare cyclododecanone by a rearrangement reaction performed under an alkali metal halide catalyst, and thus, the present invention is intended to be suggested.

Hereinafter, the method of preparing cyclododecanone of the present invention will be described in detail.

The method of preparing cyclododecanone according to an exemplary embodiment of the present invention may include: (1) applying heat while additionally injecting hydrogen peroxide to a mixture of cyclododecene and hydrogen peroxide under a catalyst system including a tungsten compound, a phosphoric acid compound, and an amine compound to prepare epoxidized cyclododecane; and (2) preparing cyclododecanone by a rearrangement reaction from a reaction mixture including the epoxidized cyclododecane under an alkaline metal halide catalyst. Here, the reaction mixture including epoxidized cyclododecane may be used without an additional separation/purification process in step (1).

Specifically, in the method of preparing cyclododecanone according to the present invention, the form of adding hydrogen peroxide may be in the form of additionally introducing hydrogen peroxide continuously to a reactor including a mixture mixed with 10 parts by weight or less of hydrogen peroxide, based on 100 parts by weight of the cyclododecene.

The improvement of conversion rate and selectivity according to the present invention depends on the form of adding hydrogen peroxide described above, but it is noted in the present invention that the effect is surprisingly improved depending on the mole ratio of the total injected amount of hydrogen peroxide (based on cyclododecanone) and the flow rate of the injection.

In the method of preparing cyclododecanone according to an exemplary embodiment of the present invention, the hydrogen peroxide additionally injected is characterized by following the addition form described above, and when the injection is performed to satisfy the following relation formula, surprisingly improved conversion rate and selectivity may be implemented.

$$50 \leq In_f \leq 150$$

$$1.0 \leq In_m \leq 3.0 \quad \text{[Relation Formula]}$$

wherein $In_f$ is a flow rate (μl/min) of the hydrogen peroxide (B) additionally injected, and $In_m$ is a mole ratio (B/A) between cyclododecene (A) and hydrogen peroxide additionally injected (B).

$In_f$ may satisfy a flow rate of, specifically 60 to 140 μl/min, and more specifically 70 to 120 μl/min. Here, $In_f$ is a flow rate based on a 0.1 L reactor, and may follow a quantitatively increased flow rate numerical value depending on an increase in a reactor volume.

As an example, the hydrogen peroxide (B) additionally injected may be injected at a flow rate described above to the reactor including a reaction solution by a pump.

As an example, the hydrogen peroxide may be pure hydrogen peroxide or an aqueous hydrogen peroxide solution, and the aqueous hydrogen peroxide solution may have a concentration of 30 wt %, 34.5 wt %, 50 wt %, or the like.

In addition, $In_m$ may satisfy a mole ratio (B/A) of 1.5 to 2.5, and more specifically a mole ratio (B/A) of 2.0 to 2.4.

When the relation formula described above is not satisfied, production of an excessive amount of reaction by-products is caused, decomposition of hydrogen peroxide is accelerated, and selectivity to epoxidation (selectivity of hydrogen peroxide) is decreased to show unfavorable efficiency, which is thus not preferred. In addition, supply of an excessive amount of hydrogen peroxide raises an interfacial temperature of two liquid phase systems in the process to rapidly produce reaction by-products in a peroxidized form, which is thus not preferred.

When the relation formula described above is not satisfied, the reaction by-products produced may be cyclododecanol, cyclododecandiol, and the like. Thus, the cyclododecene or the mixture including cyclododecene which is a starting material of the method of preparing cyclododecanone according to an exemplary embodiment of the present invention may include substantially no cyclododecane.

In the method of preparing cyclododecanone according to an exemplary embodiment of the present invention, 1 to 10 parts by weight of hydrogen peroxide may be mixed in the mixture, based on 100 parts by weight of the cyclododecene, and specifically 1 to 8 parts by weight, and more specifically 1 to 5 parts by weight of hydrogen peroxide may be mixed with the cyclododecene. A small amount of hydrogen peroxide included in the mixture may be used not as an oxidizing agent but for maximizing catalyst activity. Thus, when the amount of hydrogen peroxide included in the mixture is out of the range described above, the catalyst activity is deteriorated, which is thus not preferred.

In the method of preparing cyclododecanone according to an exemplary embodiment of the present invention, the tungsten compound which may be included in the catalyst system may be one or a mixture of two or more selected from a tungstic acid, a tungstate salt, and the like.

An example of the tungsten compound may include a tungstic acid in a monohydrate form or a dihydrate form of tungsten trioxide; a tungstate salt such as sodium tungstate, potassium tungstate, calcium tungstate, and ammonium tungstate; and the like.

As an example, when the tungsten compound included in the catalyst system includes the tungstic acid described above, the catalyst system may be in the form of a heterogeneous catalyst system.

As an example, when the tungsten compound included in the catalyst system includes one or a mixture of two or more selected from the tungstate salts described above, the catalyst system may be in the form of a homogeneous catalyst system.

As an example, when the catalyst system includes both the tungstic acid described above and the tungstate salt described above, a more improved conversion rate may be implemented.

In the method of preparing cyclododecanone according to an exemplary embodiment of the present invention, the phosphoric acid compound which may be included in the catalyst system may be one or a mixture of two or more selected from an inorganic phosphoric acid, an inorganic phosphate salt, an organic phosphoric acid, and the like.

An example of the phosphoric acid compound may include an inorganic phosphoric acid such as a phosphoric acid, a polyphosphoric acid, and a pyrophosphoric acid; an inorganic phosphate salt such as sodium phosphate, potassium phosphate, ammonium phosphate, sodium hydrogen phosphate, potassium hydrogen phosphate, ammonium hydrogen phosphate, sodium dihydrogen phosphate, potassium dihydrogen phosphate, and calcium dihydrogen phosphate; an organic phosphoric acid such as monomethyl phosphoric acid, dimethyl phosphoric acid, trimethyl phosphoric acid, triethyl phosphoric acid, and triphenyl phosphoric acid; and the like.

In the method of preparing cyclododecanone according to an exemplary embodiment of the present invention, the amine compound which may be included in the catalyst system may be one or a mixture of two or more selected from a tertiary amine, a quaternary ammonium salt, and the like.

The amine compound may be a tertiary amine selected from trimethyl amine, dimethylethyl amine, diethylmethyl amine, butyldimethyl amine, dimethylisopropyl amine, triethyl amine, tripropyl amine, tributyl amine, tripentyl amine, triisoamyl amine, trihexyl amine, triheptyl amine, trioctyl amine, tri-(2-ethylhexyl) amine, and the like; a quaternary ammonium salt selected from a dodecyltrimethyl ammonium salt, a hexadecyltrimethyl ammonium salt, an octadecyltrimethyl ammonium salt, a methyltributyl ammonium salt, a methyltrioctyl ammonium salt, and the like; and the like.

Specifically, in the step (1) of preparing epoxidized cyclododecane, oxidation is performed in a two-liquid phase system consisting of one liquid phase including cyclododecene and another liquid phase including an aqueous hydrogen peroxide solution, and it is preferred that the two-liquid phase system rapidly generates phase separation after reaction completion. Thus, it is preferred that the amine compound included in the catalyst system includes long chain alkyl having 7 or more carbon atoms.

In the method of preparing cyclododecanone according to an exemplary embodiment of the present invention, 0.001 to 10 parts by weight of the catalyst system may be included, based on 100 parts by weight of the cyclododecene, and specifically 0.01 to 5 parts by weight, and more specifically 0.1 to 1.0 part by weight of the catalyst system may be included.

In the method of preparing cyclododecanone according to an exemplary embodiment of the present invention, the tungsten compound (a), the phosphoric acid compound (b), and the amine compound (c) in the catalyst system may be mixed at a weight ratio (a:b:c) of 1:0.1 to 2.0:0.1 to 5.0. The weight ratio (a:b:c) may be specifically 1:0.5 to 1.5:0.5 to 3.0, and more specifically 1:0.8 to 1.0:1.0 to 2.5.

In the method of preparing cyclododecanone according to an exemplary embodiment of the present invention, the step (1) of preparing epoxidized cyclododecane may be performed under a temperature condition of 50 to 120° C.

As an example, the step (1) may be performed under a temperature condition of 60 to 100° C. for 0.5 to 12 hours.

As an example, the step (1) may be performed under a temperature condition of 70 to 90° C. for 2 to 8 hours.

In addition, in the method of preparing cyclododecanone according to an exemplary embodiment of the present invention, the step (2) of preparing cyclododecanone by a rearrangement reaction may be performed under an alkali metal halide catalyst.

An example of the alkali metal halide catalyst may include KI, NaI, LiI, NaCl, KCl, LiCl, NaBr, KBr, LiBr, and the like, and may be used as one or a mixture of two or more selected therefrom, of course.

The step (2) of preparing cyclododecanone by a rearrangement reaction may be performed without a solvent. In addition, it is preferred that the step (2) is performed under an inert gas atmosphere.

The inert gas is not limited as long as it is common, and an example thereof may be one or a mixed gas of two or more selected from a helium gas, an argon gas, a nitrogen gas, a neon gas, and the like.

In addition, the step (2) of preparing cyclododecanone by a rearrangement reaction may use an unpurified reaction mixture including epoxidized cyclododecane obtained from the step (1) described above. Thus, the step (2) may implement improved conversion rate and selectivity.

The reaction mixture including epoxidized cyclododecane obtained from the step (1) has a desirable effect on the conversion rate and the selectivity in the subsequent step (2).

As an example, in the step (1), the conversion rate of the cyclododecene may be 90% or more, specifically 95% or more and 99.9% or less, and more specifically 98% or more and 99.99% or less.

As an example, in the step (2), the conversion rate of the epoxidized cyclododecane may be 90% or more, specifically 95% or more and 99.9% or less, and more specifically 98% h or more and 99.99% or less.

As an example, the reaction mixture including the epoxidized cyclododecane obtained from the step (1) does not involve an additional separation/purification process after completing the step (1), and the subsequent step (2) may proceed as a continuous process. Thus, the present invention may provide a more simplified process.

The step (2) of preparing cyclododecanone by a rearrangement reaction may include 0.01 to 10 parts by weight of the alkali metal halide catalyst, based on 100 parts by weight of the epoxidized cyclododecane. Specifically, the alkali metal halide catalyst may be included at 0.1 to 5 parts by weight, and more specifically 0.5 to 3 parts by weight.

In the method of preparing cyclododecanone according to an exemplary embodiment of the present invention, the step (2) of preparing cyclododecanone by a rearrangement reaction may be performed under a temperature condition of 100 to 300° C.

As an example, the step (2) may be performed under a temperature condition of 120 to 250° C. for 0.5 to 8 hours.

As an example, the step (2) may be performed under a temperature condition of 150 to 230° C. for 0.5 to 6 hours.

As described above, the method of preparing cyclododecanone according to the present invention imparts a high conversion rate and a high selectivity as an intermediate step for preparing laurolactam. Specifically, the conversion rate to cyclododecanone by the cyclododecene amounts to at least 90%, and the high conversion rate as such may correspond to a conversion rate which is significant as compared with the conventional technology. With the remarkableness of the effect as such, the method of preparing cyclododecanone according to the present invention is expected to be usefully utilized in the application to a process system for commercialization of laurolactam.

Hereinafter, an exemplary embodiment adopting the preparation method of the present invention described above will be described in detail.

As an exemplary embodiment, the method of preparing cyclododecanone described above may be adopted as an intermediate step in the preparation of laurolactam.

Specifically, a method of preparing laurolactam may include (1) applying heat while additionally injecting hydrogen peroxide to a mixture of cyclododecene and hydrogen peroxide under a catalyst system including a tungsten compound, a phosphoric acid compound, and an amine compound, to prepare epoxidized cyclododecane; (2) preparing cyclododecanone by a rearrangement reaction from a reaction mixture including the epoxidized cyclododecane under a alkali metal halide catalyst; (3) preparing cyclododecanone oxime from the cyclododecanone by an ammonolysis oxidation reaction; and (4) preparing laurolactam from the cyclododecanone oxime by a Beckmann rearrangement reaction.

The method of preparing laurolactam according to an exemplary embodiment of the present invention imparts an excellent effect to the conversion rate to the final step by adopting the method of preparing cyclododecanone of the present invention described above. Here, the conversion rate to the final step refers to a conversion rate at total steps including the step (1) to the step (4).

Specifically, in the method of preparing laurolactam according to an exemplary embodiment of the present invention, laurolactam to be desired may be provided at a conversion rate to the final step of 90% or more which is significantly improved.

In the step (3) of preparing cyclododecanone oxime, a catalyst including ammonia; hydrogen peroxide; titanium silicalite, and the like; and a reaction activator including ammonium acetate and the like are reacted with cyclododecanone in a solvent phase including ethanol to prepare cyclododecanone oxime.

As an example, in the step (3), cyclododecanone, the catalyst, and the reaction activator are mixed with a solvent including ethanol in a reactor, and then an ammonia gas may be injected up to 1.3 to 2.5 bar in the reactor. Thereafter, hydrogen peroxide in the reactor may be injected at a flow rate of 0.5 to 3.5 ml/min by a pump.

As an example, the step (3) may be performed under a temperature condition of 50 to 100° C. for 15 to 70 minutes.

In the method of preparing laurolactam according to an exemplary embodiment of the present invention, the step (3) of preparing cyclododecanone oxime may have a conversion rate from cyclododecanone of 99% or more, specifically 99 to 99.99%.

In the step (4) of preparing laurolactam, laurolactam may be prepared by a Beckmann rearrangement reaction using cyclododecanone oxime prepared by the preparation method described above.

The Beckmann rearrangement reaction may be performed using a catalyst system in which a main catalyst including cyanuric chloride and the like and a cocatalyst including zinc chloride and the like are mixed.

As an example, the step (4) may be performed under a temperature condition of 70 to 130° C. for 1 to 20 minutes, in a solvent phase including isopropyl cyclohexane and the like.

In the method of preparing laurolactam according to an exemplary embodiment of the present invention, the step (4) of preparing cyclododecanone oxime may have a conversion rate from cyclododecanone oxime of 99% or more, specifically 99 to 99.99%.

In addition, in the method of preparing laurolactam according to an exemplary embodiment of the present invention, the selectivity of laurolactam may be 99% or more, specifically 99 to 99.99%.

Hereinafter, the novel method for preparing laurolactam including an intermediate step using the epoxidized cyclododecane according to the present invention as an intermediate will be described in detail, by the following Examples. However, the following exemplary embodiments are only a reference for describing the present invention in detail, and the present invention is not limited thereto, and may be implemented in various forms.

In addition, unless otherwise defined, all technical terms and scientific terms have the same meanings as those commonly understood by a person skilled in the art to which the present invention pertains. The terms used herein are only for effectively describing a certain exemplary embodiment, and not intended to limit the present invention.

Further, unless otherwise stated, the unit of a used amount herein may be g.

Example 1

Step 1. Method of Preparing Epoxidized Cyclododecane

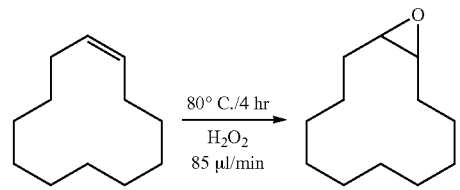 [SMILES: C1=C\CCCCCCCCCC/1 ; C1CCCCCC2OC2CCCC1]

To a high speed stirring batch reactor (100 ml), 25 g of cyclododecene, 0.075 g of $H_2WO_4$, 0.06 g of $H_3PO_4$, 0.105 g of tri-n-octyl amine, 1.4 g of $H_2O$, and 1.02 g of 50 wt % $H_2O_2$ were added. Thereafter, the reaction was performed at 80° C. for a total of 4 hours. During the reaction, hydrogen peroxide (50 wt % in water) was additionally injected at 85 µl per minute by a pump while stirring the content of the reactor at 1500 rpm.

The conversion rate of cyclododecene according to the preparation method above was 98.8%, and the selectivity was 99.9%.

Step 2. Method of Preparing Cyclododecanone

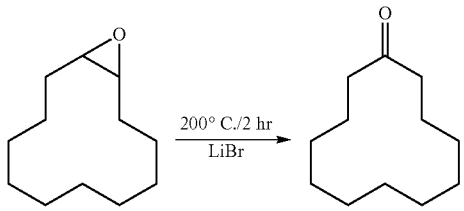

To a 50 ml round flask, 5 g of a reaction mixture including epoxidized cyclododecane obtained in step 1 and 0.085 g of lithium bromide (LiBr) were added under an inert condition using a glovebox. Thereafter, a nitrogen balloon was made and connected to the flask, which was placed in an oil bath including a silicone oil to perform the reaction at 200° C. for a total of 2 hours.

The conversion rate of epoxidized cyclododecane according to the method above was 99.5%, and the selectivity was 99.8%.

Examples 2 to 6

As shown in the following Table 1, the added amount and the addition form of hydrogen peroxide were adjusted and each reaction was performed in the similar manner as in Example 1.

As a result, the conversion rate and the selectivity in each step are shown in the following Table 2.

TABLE 1

| Step 1. | Mixture[1] (g) | Flow rate (µl/min) | Hydrogen peroxide[2] Total amount of injection[3] (g) | $In_m$ |
|---|---|---|---|---|
| Example 1 | 25:1.02 | 85 | 24.48 | 2.39 |
| Example 2 | 25:0.1 | 85 | 24.48 | 2.39 |
| Example 3 | 25:5.6 | 85 | 24.48 | 2.39 |
| Example 4 | 25:40 | 45 | 12.96 | 2.53 |
| Example 5 | 25:1.02 | 40 | 12.96 | 2.53 |
| Example 6* | 25:1.02 | 160 | 12.96 | 3.38 |

Mixture[1]: a mixture of cyclododecene and 50 wt % hydrogen peroxide, used amount of each component
Hydrogen peroxide[2]: hydrogen peroxide additionally injected
Total amount of injection: total amount of injection (B) of hydrogen peroxide additionally injected
$In_m$: a mole ratio of (B), based on cyclododecene (A) (B/A)
Example 6*: a reaction time of 1.5 hours

TABLE 2

|  | Conversion rate[1] | Selectivity[2] |
|---|---|---|
| Example 1 | 99.5 | 99.8 |
| Example 2 | 90.1 | 91.7 |
| Example 3 | 90.3 | 90.3 |
| Example 4 | 86.2 | 82.4 |

TABLE 2-continued

|  | Conversion rate[1] | Selectivity[2] |
|---|---|---|
| Example 5 | 90.2 | 90.0 |
| Example 6 | 90.7 | 90.0 |

Conversion rate[1] and selectivity[2] are in a range of meaning for epoxidized cyclododecane according to step 2.

Example 7

Step 1. Method of Preparing Epoxidized Cyclododecane

To a high speed stirring batch reactor (100 ml), 25 g of cyclododecene, 0.1 g of $Na_2WO_4$, 0.06 g of $H_3PO_4$, 0.12 g of aliquot 336 (cognis), 1.4 g of $H_2O$, and 1.02 g of 50 wt % $H_2O_2$ were added. Thereafter, the reaction was performed at 80° C. for a total of 4 hours. During the reaction, hydrogen peroxide was additionally injected at 85 µl per minute by a pump while stirring the content of the reactor at 1500 rpm.

The conversion rate of cyclododecene according to the preparation method above was 96.0%, and the selectivity was 98.1%.

Step 2. Method of Preparing Cyclododecanone

The reaction was performed in the same manner as in step 2 of Example 1, using the reaction mixture including epoxidized cyclododecane obtained in step 1.

The conversion rate of epoxidized cyclododecane according to the preparation method above was 99.0%, and the selectivity was 99.3%.

Example 8

Step 1. Method of Preparing Epoxidized Cyclododecane

To a high speed stirring batch reactor (100 ml), 25 g of cyclododecene, 0.075 g of $H_2WO_4$, 0.06 g of $H_3PO_4$, 0.12 g of aliquot 336 (cognis), 1.4 g of $H_2O$, and 1.02 g of 50 wt % $H_2O_2$ were added. Thereafter, the reaction was performed at 80° C. for a total of 4 hours. During the reaction, hydrogen peroxide was additionally injected at 85 µl per minute by a pump while stirring the content of the reactor at 1500 rpm.

The conversion rate of cyclododecene according to the method above was 99.8%, and the selectivity was 98.8%.

Step 2. Method of Preparing Cyclododecanone

The reaction was performed in the same manner as in step 2 of Example 1, using the reaction mixture including epoxidized cyclododecane obtained in step 1.

The conversion rate of epoxidized cyclododecane according to the preparation method above was 99.2%, and the selectivity was 99.0%.

Comparative Example 1

The process was performed in the same manner as in Example 1, except that the total used amount of hydrogen peroxide used in step 1 of Example 1 was mixed initially in the reactor to perform the reaction.

In this case, explosive gas by hydrogen peroxide was produced to increase the temperature, and thus, the reaction had to be finished in the middle.

As shown in the Examples, it was confirmed that according to the present invention, cyclododecanone may be prepared at a high conversion rate and a high selectivity from cyclododecene. In particular, when the flow rate and the total used amount of hydrogen peroxide additionally injected satisfied the relation formula described above, it was confirmed that a surprisingly improved effect to the conversion rate and the selectivity is shown.

In addition, when the amount of hydrogen peroxide mixed initially in the reactor in step 1 was small, it was confirmed that the conversion rate may be somewhat decreased by the influence of the catalyst formation. In addition, when the amount of hydrogen peroxide mixed initially in the reactor in step 1 was excessive, it was confirmed that the selectivity to epoxidation is decreased by decomposition of hydrogen peroxide even in the case of using the same total amount of hydrogen peroxide, thereby decreasing the total conversion rate.

As confirmed in the above Examples, according to the present invention, not only unreacted materials but also reaction by-products are minimized, so that a separation/purification process for removing the reaction by-products is also unnecessary. Thus, the present invention provides a simplified process configuration, and is advantageous for commercial mass production.

In summary, according to the present invention, since cyclododecanone may be provided at high conversion rate and a high selectivity under very economical condition, by the simplified process configuration, the present invention is expected to be usefully utilized in application to a process system for commercialization of laurolactam.

Hereinabove, although the present invention has been described by specified matters and specific exemplary embodiments, they have been provided only for assisting in the entire understanding of the present invention, and the present invention is not limited to the exemplary embodiments. Various modifications and changes may be made by those skilled in the art to which the present invention pertains from this description.

Therefore, the spirit of the present invention should not be limited to the above-described exemplary embodiments, and the following claims as well as all modified equally or equivalently to the claims are intended to fall within the scope and spirit of the invention.

The invention claimed is:

1. A method of preparing cyclododecanone, the method comprising: applying heat while additionally injecting hydrogen peroxide to a mixture of cyclododecene and hydrogen peroxide under a catalyst system including a tungsten compound, a phosphoric acid compound, and an amine compound to prepare epoxidized cyclododecane; and preparing cyclododecanone by a rearrangement reaction without separation of a reaction mixture including the epoxidized cyclododecane under an alkaline metal halide catalyst, wherein the hydrogen peroxide additionally injected is injected is injected so that the following relation formula is satisfied:

$$50 \leq In_f \leq 150$$

$$1.0 \leq In_m \leq 3.0$$ [Relation Formula]

wherein $In_f$ is an injection flow rate per minute (μl/min) of the hydrogen peroxide additionally injected based on a 0.1 L reactor, and $In_m$ is a mole ratio (B/A) between cyclododecene (A) and hydrogen peroxide additionally injected (B).

2. The method of preparing cyclododecanone of claim 1, wherein the mixture includes substantially no cyclododecane.

3. The method of preparing cyclododecanone of claim 1, wherein 1 to 10 parts by weight of the hydrogen peroxide is mixed, based on 100 parts by weight of the cyclododecene.

4. The method of preparing cyclododecanone of claim 1, wherein the tungsten compound is a tungstic acid, a tungstate salt, or a mixture thereof.

5. The method of preparing cyclododecanone of claim 1, wherein the phosphoric acid compound is an inorganic phosphoric acid, an inorganic phosphate salt, an organic phosphoric acid, or a mixture thereof.

6. The method of preparing cyclododecanone of claim 1, wherein the amine compound is a tertiary amine, a quaternary ammonium salt, and a mixture thereof.

7. The method of preparing cyclododecanone of claim 1, wherein 0.001 to 10 parts by weight of the catalyst system is included, based on 100 parts by weight of the cyclododecene.

8. The method of preparing cyclododecanone of claim 7, wherein in the catalyst system, the tungsten compound (a), the phosphoric acid compound (a), and the amine compound (c) are mixed at a weight ratio of 1:0.1 to 2.0:0.1 to 5.0.

9. The method of preparing cyclododecanone of claim 1, wherein the preparing of epoxidized cyclododecane is performed under a temperature condition of 50 to 120° C.

10. The method of preparing cyclododecanone of claim 1, wherein the rearrangement reaction is performed without a solvent.

11. The method of preparing cyclododecanone of claim 1, wherein 0.01 to 10 parts by weight of the alkali metal halide catalyst is included, based on 100 parts by weight of the epoxidized cyclododecane.

12. The method of preparing cyclododecanone of claim 1, wherein a conversion rate of the cyclododecene and a conversion rate of the epoxidized cyclododecane are 90% or more.

* * * * *